United States Patent
Steen et al.

(10) Patent No.: US 6,485,735 B1
(45) Date of Patent: *Nov. 26, 2002

(54) MULTILAYER THERMOSET POLYMER MATRIX AND STRUCTURES MADE THEREFROM

(75) Inventors: Brett Steen, Ooltewah, TN (US); Floyd Gold, Wildwood, GA (US); Stevie Daniel, Trenton, GA (US)

(73) Assignee: Phelps Dodge High Performance Conductors of SC & GA, Inc., Inman, SC (US)

(*) Notice: Subject to any disclaimer, the term of this patent is extended or adjusted under 35 U.S.C. 154(b) by 0 days.

This patent is subject to a terminal disclaimer.

(21) Appl. No.: 09/400,419

(22) Filed: Sep. 21, 1999

Related U.S. Application Data

(63) Continuation-in-part of application No. 09/387,528, filed on Aug. 31, 1999, now Pat. No. 6,213,995.

(51) Int. Cl.[7] .............................. A61F 2/00; A61K 9/70; A61K 9/14
(52) U.S. Cl. ...................... 424/423; 424/422; 424/443; 424/484
(58) Field of Search ................. 424/422, 423, 424/443, 484; 623/1.1, 1.11, 1.44, 1.46

(56) References Cited

U.S. PATENT DOCUMENTS

| | | | |
|---|---|---|---|
| 4,086,297 A | 4/1978 | Rei et al. ............... 260/859 PV |
| 4,923,450 A | * 5/1990 | Maeda et al. ................ 604/265 |
| 4,935,232 A | 6/1990 | McIntosh ..................... 424/78 |
| 5,043,280 A | 8/1991 | Fischer et al. ........... 435/235.1 |
| 5,238,749 A | 8/1993 | Cueman et al. ............. 428/441 |
| 5,300,048 A | * 4/1994 | Drewes, Jr. et al. ........ 604/280 |
| 5,310,557 A | 5/1994 | Brandt et al. ................ 424/411 |
| 5,320,908 A | 6/1994 | Sodervall et al. ........... 428/461 |
| 5,358,979 A | 10/1994 | van Hoboken .............. 523/122 |
| 5,366,727 A | 11/1994 | Kanazawa et al. ........ 424/78.35 |
| 5,478,563 A | 12/1995 | Erami ........................ 424/409 |
| 5,630,806 A | * 5/1997 | Inagaki et al. ............... 604/282 |
| 5,688,516 A | 11/1997 | Raad et al. .................. 424/409 |
| 5,698,229 A | 12/1997 | Ohsumi et al. ............. 424/604 |
| 5,744,151 A | 4/1998 | Capelli ........................ 424/405 |
| 5,817,325 A | 10/1998 | Sawan et al. ................ 424/411 |
| 5,827,524 A | 10/1998 | Hagiwara et al. ........... 424/409 |
| 5,837,313 A | * 11/1998 | Ding et al. ................. 427/2.21 |
| 5,849,311 A | 12/1998 | Sawan et al. ................ 424/406 |
| 5,869,073 A | 2/1999 | Sawan et al. ................ 424/406 |
| 5,873,904 A | * 2/1999 | Ragheb et al. .................. 623/1 |
| 5,885,603 A | 3/1999 | Fowler et al. .............. 424/405 |
| 5,906,825 A | 5/1999 | Seabrook, Jr. .............. 424/404 |
| 6,015,613 A | * 1/2000 | Kinlen et al. ................ 428/332 |
| 6,179,817 B1 | * 1/2001 | Zhong ........................ 604/265 |
| 6,267,782 B1 | * 7/2001 | Ogle et al. .................... 623/1.1 |

* cited by examiner

*Primary Examiner*—Thurman K. Page
*Assistant Examiner*—Rachel M. Bennett
(74) *Attorney, Agent, or Firm*—David P. Gordon; David S. Jacobson; Thomas A. Gallagher

(57) ABSTRACT

A composite thermoset polymer matrix structure having a plurality of homogeneously bonded thermoset polymer layers and a method of forming the same is disclosed. Each of the layers is formed from either a pure thermoset polymer resin or a composition of any of a variety of thermoset polymer resins and any of a variety of agents or combination of agents heterogeneously dispersed and suspended within the thermoset polymer resin. In this manner, each layer exhibits a distinct desirable functional property or characteristic depending upon an intended application. The agents are selected from a group of additives including but not limited to anti-microbial agents, anti-fungal agents, anti-viral agents, anti-thrombotic agents, friction reducing agents; radiopaque agents, and electrically conductive or resistive agents. The composite thermoset polymer matrix structure may be formed into any size or any shape, object, or structure.

38 Claims, 4 Drawing Sheets

MULTILAYER THERMOSET POLYMER MATRIX AND STRUCTURES MADE THEREFROM

This application is a continuation-in-part of U.S. Ser. No. 09/387,528 filed Aug. 31, 1999 now U.S. Pat. No. 6,213, 995, entitled "Flexible Tubing with Braided Transmission Elements", which is hereby incorporated by reference herein in its entirety.

BACKGROUND OF THE INVENTION

1. Field of the Invention

This invention relates broadly to polymer matrix compositions. More particularly, this invention relates to a thermoset polymer matrix having multiple layers, each formed from any of a variety of thermoset polymer resins and having any of a variety of functional agents suspended within the resin.

2. State of the Art

Polymer resin technology and methods of forming structures using thermoset resins are well known in the prior art. Thermoset polymer materials and equipment are commonly used in the medical industry as well as in other industries. Embedding or coating such structures with anti-microbial agents is also known in the industry. For example, U.S. Pat. No. 5,817,325 of Sawan et al. discloses contact killing anti-microbial articles, devices and formulations whose contact killing properties can be applied to the surface of an object or are contained within an article which is intended to contact biological tissues. The antimicrobial layer is either applied secondarily to the article or device or cast into the article or device as the article or device is formed. Sawan teaches that the anti-microbial material is an organic polycationic polymer matrix such as a biguanide polymer having bound or complexed thereto a surface-accessible anti-microbial metallic material (biocide). The polymer matrix must be capable of reversibly binding or complexing with the biocide and also be capable of subtly infusing the biocide into the cell membrane of the microorganism. According to Sawan, it is preferable that the organic material be capable of dissolving into or adhering to the microorganism's cell membrane.

U.S. Pat. No. 5,478,563 to Erami discloses an antibacterial and anti-fungal composition formed from a polyacetal base resin and antibacterial and/or anti-fungal agents melt-blended or directly added to the polyacetal base resin such that resin and agents completely combine to form a homogeneous resin mixture; i.e., a mixture in which the agents are soluble and dissolve into the resin.

U.S. Pat. No. 5,827,524 to Hagiwara et al. discloses a porous crystalline anti-microbial polymer composition which is coated on a silica gel substrate, heated, and then sintered to form, or which may then be mixed with a polymer to provide the polymer structure with antimicrobial properties. The polymer structure is thereby uniformly provided throughout its thickness, with the antimicrobial polymer composition. As such, the antimicrobial composition, which is relatively expensive, is even provided in central portions of the structure, where it cannot act against microbial agents.

SUMMARY OF THE INVENTION

It is therefore an object of the present invention to provide a composite thermoset structure having a plurality of thermoset polymer matrix layers.

It is another object of the invention to provide a composite thermoset polymer matrix having one or more agents heterogeneously suspended therein, where the polymer matrix can then be utilized in a structure.

It is an additional object of the present invention to provide composite thermoset polymer matrix structures having a plurality of polymer matrix layers homogeneously bonded together, where each layer is formed from a composition of any of a variety of thermoset polymer resins and any of a variety of agents or combination of agents heterogeneously dispersed within the thermoset polymer resin such that each layer exhibits a distinct desirable functional property or characteristic.

It is a further object of the present invention to provide a composite thermoset polymer structure having a plurality of homogeneously bonded thermoset polymer matrix layers with each layer exhibiting any of a variety of distinct desirable properties including but not limited to anti-microbial properties, anti-fungal properties, anti-viral properties, anti-thrombotic properties, friction reducing properties, radiopacity properties, and thermo-electrical resistance or conductive properties.

Another object of the invention is to provide a great variety of composite thermoset polymer matrix structures including tubes, sheets, wire coatings, and tapes which have any of a variety of desirable properties included within a polymer matrix structure.

In accord with these objects, which will be discussed in detail below, a composite thermoset polymer matrix structure has a plurality of homogeneously bonded thermoset polymer layers; i.e., each layer is bonded to the other such that the plurality of layers mechanically functions as a single layer. Such homogeneous bonding is a combination of adhesion, cross-linking, and hydrogen bonding. Each of the layers is formed from either a pure thermoset polymer resin or a composition of any of a variety of thermoset polymer resins and any of a variety of agents or combination of agents heterogeneously dispersed and suspended within the thermoset polymer resin. In this manner, each layer exhibits a distinct desirable functional property or characteristic depending upon an intended application. Various structures such as a polymer tape, wire coating, sheet and tube are provided. In forming the structures, each layer of the structure is preferably formed from a plurality (typically numerous) sublayers, all of the same composition.

It will be appreciated that the composite thermoset polymer matrix structure may be formed into any size or any shape, object, or structure. It will further be appreciated that the arrangement and composition of the homogeneously bonded composite thermoset polymer matrix layers may be varied depending upon the desirable qualities, properties, or characteristics required by the intended application.

The thermoset polymer resin used to form the composite thermoset polymer matrix layers of the present invention may be selected from any of a plurality of thermoset polymer resins which have homogeneous bonding characteristics including but not limited to polyimide, polyurethane, polyester, polyamide-imide, and polyamide. According to the preferred embodiment the thermoset polymer resin used to form the matrix is polyimide.

According to one aspect of the invention, the agents dispersed and suspended in each layer of the polymer matrix are selected from a group of additives including but not limited to anti-microbial agents, anti-fungal agents, anti-viral agents, anti-thrombotic agents, friction reducing agents, radiopaque agents, and electrically conductive or resistive agents. Any of a variety of anti-microbial agents may be added to the thermoset polymer resin, but silver ion producing agents carried in a zeolite carrier are preferred. Likewise, any of a variety of anti-fungal agents, anti-viral agents, anti-thrombotic agents, etc. can be utilized. While the radiopaque agents, and the electrically conductive agents, may be added to any layer within the matrix structure, it is preferable that the anti-microbial agents, the anti-fungal agents, the anti-viral agents, the anti-thrombotic agents, and the friction reducing agents be added to an exposed surface layer of the matrix.

According to another aspect of the invention, the agents suspended in the matrix remain in powder form, have a particulate size (diameter) of up to 5 microns, and constitute up to thirty percent by weight of the finished solid plastic material.

A method of forming the composite thermoset polymer matrix is also provided. The method of forming a solid plastic structure from a thermosetting polymer resin or resin suspension generally includes applying a liquid polymer resin to an object or forming a layer coated on a mandrel, and heating the polymer resin until it cures to form a first layer. If multiple sublayers of the same resin are desired, the process is repeated. Once a first thermoset polymer resin layer is cured, additional thermoset polymer resin layers may be applied to it using the same technique detailed above.

According to the invention, at least one of the layers is provided with an agent additive heterogeneously suspended within the resin. This is accomplished by mixing any of a variety of liquid thermoset polymer resins with any of a variety of agents or combination of agents in a powdered particulate form until the powdered particulate is evenly dispersed throughout the liquid resin. Once evenly dispersed, a true heterogenous thermoset polymer mixture is formed. A true heterogenous mixture means that the powdered particulate added is merely suspended and encased within the liquid resin; i.e. no chemical bonding or polymerization between the powdered particulate and the resin occurs.

A composite thermoset polymer matrix sheet is formed by pouring a first layer of the liquid thermoset polymer resin (with or without additives) into the form of a flat sheet, heat curing the first layer, and then applying additional composite thermoset polymer resin suspension layers with one or more additives to the first layer as described above.

A composite thermoset polymer matrix wire coating is formed by coating a metal substrate, preferably a copper wire, with the liquid thermoset polymer resin and then heat curing the thermoset polymer resin as described above. Any number of layers with different additives may be applied to the metal substrate, one atop another, until a desired matrix thickness is achieved. A composite thermoset polymer matrix tube is produced by removing the metal substrate from within the composite thermoset polymer matrix layers after the desired matrix thickness is achieved.

The thermoset polymer matrix structures described above have numerous possible applications within a variety of technologies and industries including the medical technology industry, research and development technologies, the oil and gas industry, aviation and space exploration, and electrical design industries.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
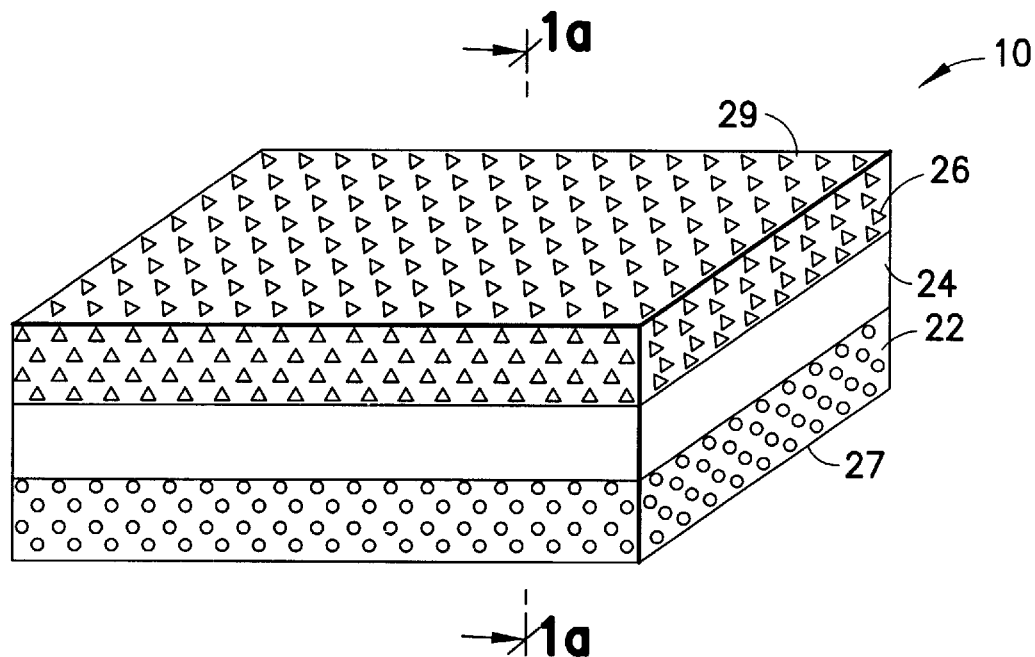
FIG. 1 is a perspective view of a first embodiment of a multi-layered composite thermoset polymer matrix formed into the shape of a sheet.

According to the invention, a composite thermoset polymer matrix structure has a plurality of homogeneously bonded thermoset polymer layers; i.e., each layer is bonded to the other such that the plurality of layers mechanically functions as a single layer. Such homogeneous bonding is preferably a combination of adhesion, cross-linking, and hydrogen bonding. Each of the layers is formed from either a pure thermoset polymer resin or a composition of any of a variety of thermoset polymer resins and any of a variety of agents or combination of agents heterogeneously dispersed and suspended within the thermoset polymer resin. In this manner, each layer exhibits a distinct desirable functional property or characteristic depending upon an intended application. In forming the structures, each layer of the structure is preferably formed from a plurality (typically numerous) sublayers, all of the same composition.

The thermoset polymer resin used to form the composite thermoset polymer matrix layers of the present invention is selected from any of a plurality of thermoset polymer resins which have homogeneous bonding characteristics including but not limited to polyimide, polyurethane, polyester, polyamide-imide, and polyamide. According to the preferred embodiment the thermoset polymer resin used to form the matrix is polyimide. However, other thermoset polymer resins can be used for all layers, or different layers may utilize different resins.

According to the invention, at least one layer of the structure includes one or more agents dispersed and suspended in the polymer matrix. The agents include but are not limited to anti-microbial agents, anti-fungal agents, anti-viral agents, anti-thrombotic agents, friction reducing agents, radiopaque agents, and electrically conductive or resistive agents.

More particularly, any of a variety of anti-microbial agents may be added to the thermoset polymer resin, including but not limited to silver ion producing agents, zinc ion producing agents, copper ion producing agents, and gold ion producing agents. In the preferred embodiment, silver ion producing agents are utilized. Any of a variety of silver ion producing agents are preferably carried in a carriers, which may include but are not limited to zeolite, hydroxyl apatite, silica gel, glass, magnesium, aluminate silicate, and partially soluble phosphates. A preferred carrier for a silver ion producing agent is zeolite.

By way of example, and not by way of limitation, anti-fungal agents include the anti-microbial agents listed above, and additionally zinc oxide, zinc benzoate, zinc sulfate, and zinc borate. By way of example and not by way of limitation, the anti-thrombotic agents include heparin, phosphorylcholine, ibuprofen, acetylsalicylic acid, dipyridamole, indomethacin, prostaglandin, sulfinpyrazone, and warfarin. By way of example and not by way of limitation, the friction reducing agents include polytetraflouroethylene (PTFE), FEP, and graphite. By way of example and not by way of limitation, the radiopaque agents include metallic tungsten, metallic barium, and metallic gold. Finally, by way of example and not by way of limitation, the electrically conductive or resistive agents which can be used to dissipate static charges and shield against electromagnetic interference include carbon black, graphite, copper, and silver.

According to the invention, the agents suspended in the matrix remain in powder form and have a particulate size (diameter) of up to 5 microns, and more preferably about 1 micron. While according to the preferred embodiment, the amount of additive added to the polymer resin constitutes up to thirty percent by weight of the finished solid plastic material, it is more preferable that the amount of additive constitute only up to fifteen percent by weight of the finished solid plastic. While the individual matrix layers may be formed in any thickness depending upon the particular requirement or intended use, it is preferable that the thickness of the matrix sublayers be between 0.00025 to 0.05 inches. More preferably, the thickness of the matrix sublayers is between 0.00025 to 0.0005 inches.

Further, while the radiopaque agents, and the electrically conductive agents, may be added to any layer within the matrix structure, it is preferable that the anti-microbial agents, the anti-fungal agents, the anti-viral agents, the anti-thrombotic agents, and the friction reducing agents be added to an exposed surface layer of the matrix.

According to the method of the invention, a thermoset polymer resin is provided in a liquid state. The thermoset polymer resin is kept in liquid form by tying up many of its primary and secondary bonding sites with solvent molecules as is well appreciated by those skilled in the art. If the polymer resin or resin is to include a heterogenous suspension, the additive is added to the liquid resin as is described in more detail hereinafter. Regardless, the liquid polymer resin (or resin suspension) is then applied to an object or mandrel for forming a layer. After the layer is coated onto the mandrel, the resin suspension is converted into a solid structure by curing (i.e., exposing to heat and thereby driving off the solvent materials within the resins and allowing polymerization and cross-linking to occur). If multiple sublayers of the same resin are desired, the process is repeated until the desired layer thickness is achieved.

Once a first thermoset polymer resin layer is cured, additional thermoset polymer resin layers may be applied using the same technique detailed above. Bonding between different sublayers and layers of the thermoset polymer resin is achieved through adhesion, cross-linking, and hydrogen bonding which occur as adjacent layers are cured on previous layers; i.e., the sublayer and layers are each homogeneously bonded to each other such that they together mechanically function as a single layer.

As suggested above, and according to the invention, at least one of the layers is provided with an agent additive heterogeneously suspended within the resin. This is accomplished by thoroughly blending any of a variety of liquid thermoset polymer resins with any of a variety of agents or combination of agents in a powdered particulate form until the powdered particulate is evenly dispersed throughout the liquid resin. Depending upon the circumstances, it may take, e.g., about six hours to evenly disperse the powdered particulate throughout the liquid resin. Once evenly dispersed, a true heterogenous thermoset polymer mixture is formed. The liquid resin suspension is considered heterogenous because the powdered particulate is merely suspended and encased within the liquid resin, i.e., no chemical bonding or polymerization between the powdered particulate and the liquid resin occurs.

Figure 1A:
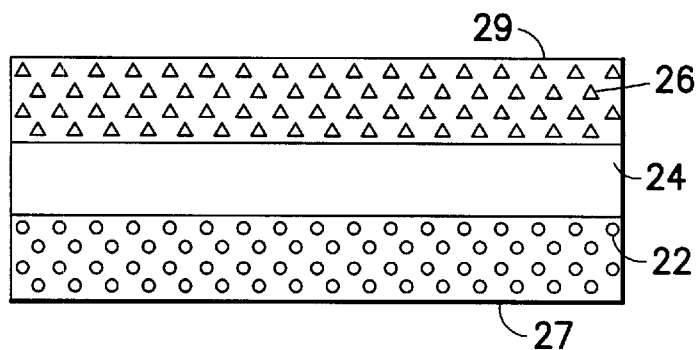
FIG. 1a is a cross-section through the sheet of FIG. 1.

Referring now to FIGS. 1 and 1a, a first embodiment of the invention is shown as a composite thermoset polymer matrix sheet 10 having three layers 22, 24, 26. The first layer 22 is comprised of a resin suspension of a first thermoset polymer resin, e.g. polyimide, and a friction reducing agent, such as PTFE. As seen in FIG. 1, the PTFE powdered particles are suspended in the resin, with at least some particles located at the exposed surface 27 of the layer and thereby providing lubricity to the surface 27 of the layer 22. The second layer 24 is comprised of a second thermoset polymer resin, e.g. polyimide, without an added agent. The second layer 24 is homogeneously bonded to the first layer 22. The third layer 26 is comprised of a third thermoset polymer resin, e.g., polyimide, and an anti-microbial agent. As seen in FIGS. 1 and 1a, the anti-microbial powdered particles are suspended in the resin, with at least some particles located at the exposed surface 29 of the third layer 26, thereby providing the sheet 10 with an anti-microbial surface. The first, second, and third thermoset polymer resins of each of the layers may be the same resin, e.g., a polyimide resin, or may be different resins, provided the resins will cross-link and/or bond to each other via hydrogen and/or adhesion bonding; i.e., homogeneously bond. Each of the layers may comprise one or more sublayers (not shown) having substantially the same composition within the layer. As will be appreciated by those skilled in the art, all vertical cross-sections through the sheet of FIG. 1 (such as the cross-section of FIG. 1a) are preferably substantially uniform.

Figure 2:
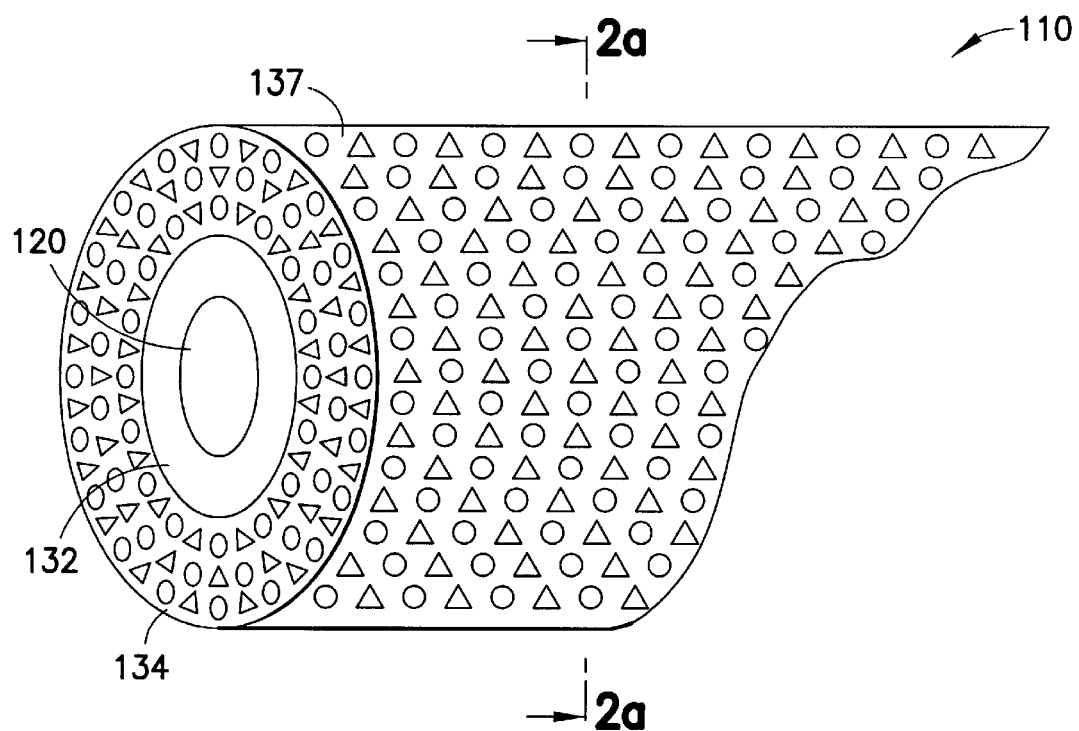
FIG. 2 is a perspective view of a second embodiment of a multi-layered composite thermoset polymer matrix formed as a coating on a metallic substrate.
Figure 2A:
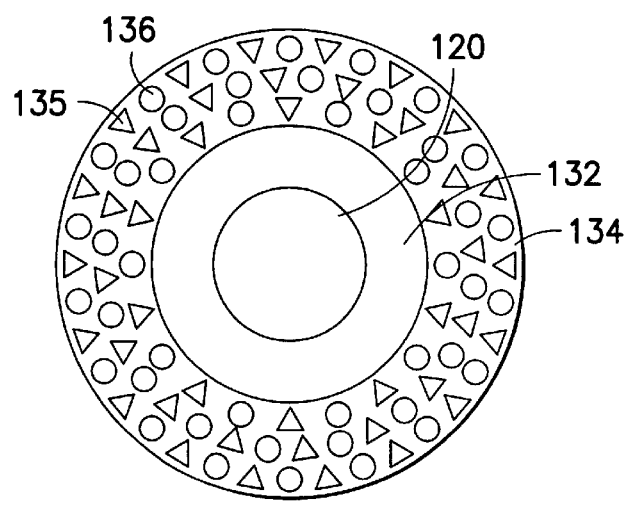
FIG. 2a is a cross-section through FIG. 2.

Referring to FIGS. 2 and 2a, according to a second embodiment of the invention, an insulated wire 110 is provided. The insulated wire 110 includes a wire substrate 120 on which first and second polymer resin layers 132 and 134 are coated. In other words, a copper or aluminum wire 120, serves as a substrate upon which the thermoset polymer matrix is provided, as well as functioning as a conductive element. A first layer 132 is formed about the wire 120 by first dipping the wire into a resin or a resin suspension to form a first sublayer of the resin or resin suspension on the wire. The first sublayer is then heated and cured into a solid form. The process may be repeated to apply one or more additional sublayers (each preferably between 0.00025–0.0005 inches thick) of the resin or resin suspension over the wire until the first layer has a desired thickness. Application of the resin or resin suspension, the curing process, and other aspects of forming a coated wire are more completely disclosed in U.S. Pat. No. 5,630,806, which is hereby incorporated by reference herein in its entirety. Following formation of a sufficiently thick first layer, additional layers may be added, each formed in a similar manner until the desired structure is formed. Each sublayer forms a homogeneous bond to adjacent sublayers such that all the sublayers which form a single layer form a relatively homogeneous structure.

Applying the principles described above, according to the second example, the first thermoset polymer layer 132 is a polyimide resin applied in sublayers directly to the wire and cured. No agent additives are added to the first resin layer. The second thermoset polymer layer 134 is a heterogenous combination of, by weight, ninety percent of polyurethane, five percent of PTFE 135, and five percent of zeolite 136. Because the PTFE and zeolite particles are suspended in the polyimide resin, with some of the particles on the surface 137 of the second layer 134, the second thermoset polymer layer provides an outer (exposed) surface having both low friction and anti-bacterial properties.

Figure 3:
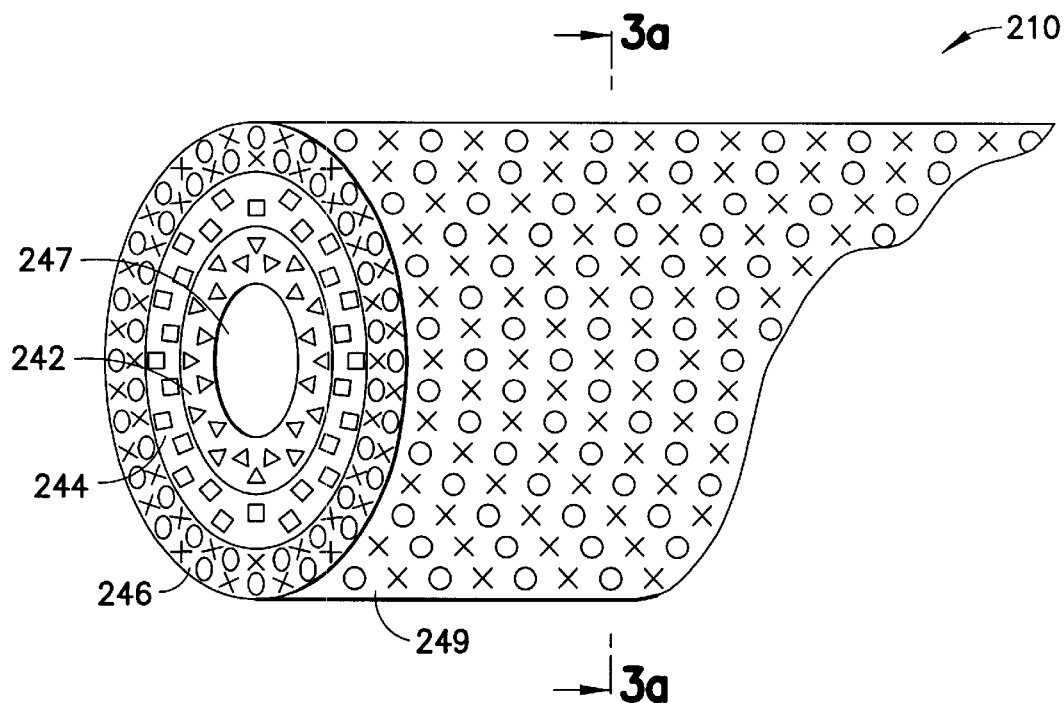
FIG. 3 is a perspective view of a third embodiment of a multi-layered composite thermoset polymer matrix formed in the shape of a tube.
Figure 3A:
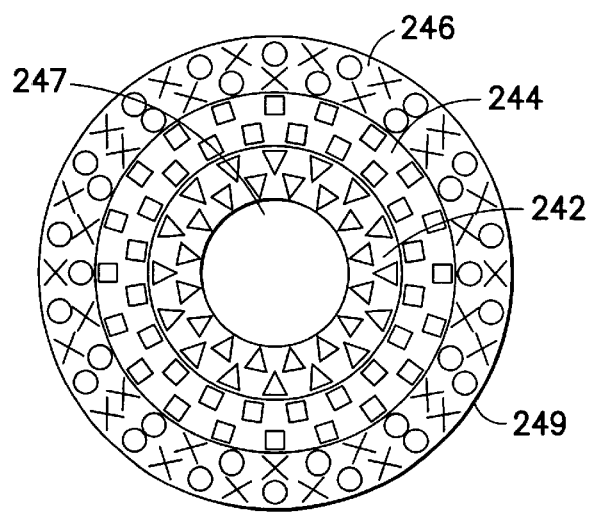
FIG. 3a is a cross-section through the tube of FIG. 3.

Referring to FIGS. 3 and 3a, a third example of a composite thermoset polymer matrix structure formed according to the invention is shown. The structure is in the form of a tube 210 having three layers 242, 244, 246. The tube structure is formed about a metallic substrate similar to the manner of coating a wire described above with reference to FIGS. 2 and 2a. When the metallic substrate is removed, such as by elongating the metallic substrate to reduce its diameter and withdrawing the substrate from the cured thermoset polymer matrix structure, the tube 210 will have a lumen which is equivalent in diameter to the initial diameter of the metallic substrate.

In forming the tube 210, and as described in greater detail above, an innermost first layer 242 of the composite thermoset polymer matrix tube is formed and cured in sublayers about a metallic substrate, or mandrel, having a diameter equivalent to the desired diameter of the polymer matrix tube. The first layer is a heterogenous mixture or suspension of a friction reducing agent, such as PTFE (20%), in a first thermoset resin, e.g. polyimide (80%), thereby providing the inner surface 247 with lubricity. The second layer 244 is a heterogenous mixture of ninety percent a second thermoset polymer resin, e.g. polyurethane, and ten percent of a tungsten powder agent added to provide radiopacity (x-ray visibility). The second layer 244 is bonded to the first layer 242 as described above. The third layer 246 is a heterogenous mixture of ninety percent of a third thermoset polymer resin, e.g. polyimide, five percent of an anti-thrombotic agent such as, heparin, and five percent of an anti-microbial agent, such as zeolite. The third layer is homogeneously bonded to the second layer and provides an exterior surface 249. Thus, the third layer 246 provides the outer tube surface 249 with anti-thrombotic and anti-bacterial properties. After the final polymer matrix layer is applied and cured, as previously mentioned, the mandrel is elongated to decrease its diameter and removed, leaving a lumen in the tube. The tube of FIGS. 3 and 3a is advantageously used, among other things, as a catheter which can be slid over a guidewire.

Figure 4:
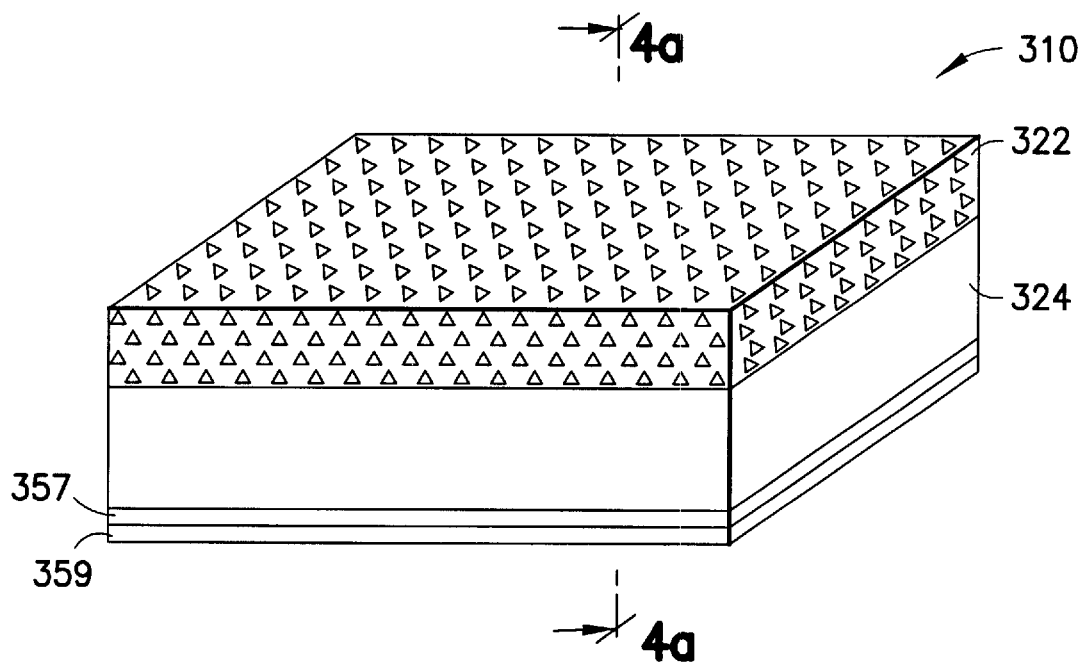
FIG. 4 is a perspective view of a fourth embodiment of a multi-layered composite polymer matrix sheet having an adhesive layer and peel-off backing applied.
Figure 4A:
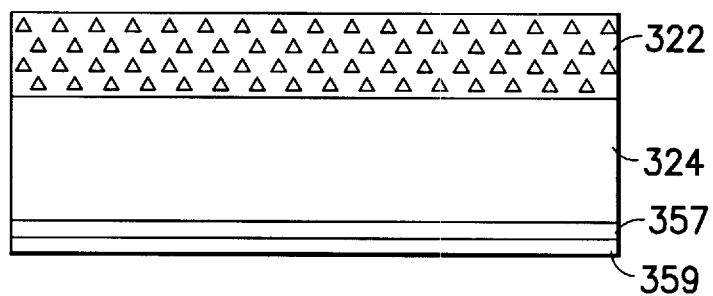
FIG. 4a is a cross-section through the adhesive sheet of FIG. 4.

Referring to FIGS. 4 and 4a, a fourth example of a composite thermoset polymer matrix structure formed according to the invention is shown. The structure is a polymer matrix tape 310 having two resin layers 322, 324, an adhesive layer 357 and a peel-off backing 359. The first layer 322, which will become an exposed surface layer, is a suspension of a friction reducing agent, such as PTFE, in a first thermoset resin, e.g., polyamide-imide. The second layer is comprised of a second thermoset polymer resin, e.g., polyimide, preferably including an anti-microbial agent suspended therein (not shown). The second layer is homogeneously bonded to the first layer as described above. A biomedical grade, hypoallergenic adhesive layer 357 is applied to the second layer 324 followed by a peel-off backing 359. When the backing 359 is removed, the tape 310 may be applied to and will adhere to a surface and provide reduced friction properties. The tape of FIGS. 4 and 4a has advantageous application for use on the body and for medical electronic encapsulation.

According to a fifth example (not shown), a composite thermoset polymer matrix tube is formed according to the invention and includes five layers. A first very thin surface layer is comprised of a suspension of polyimide resin (85%) having a silver ion releasing anti-microbial agent (5%) and an anti-thrombotic agent (10%) suspended therein. A second relatively thick layer formed from numerous sublayers is comprised of a polyimide resin without any additives. A third, relatively thin layer is comprised of a suspension of polyimide resin (88%) having a tungsten powder (12%) radiopaque additive suspended therein. A fourth relatively thick layer formed from numerous sublayers is comprised of a polyimide resin without any additives. A fifth very thin surface layer is comprised of a polyimide resin (92%) having a PTFE friction reducing agent (8%) heterogeneously suspended therein.

According to a sixth example (not shown), a composite thermoset polymer matrix tube is formed according to the invention and includes two layers. A first layer is comprised of a polyimide resin having no additives suspended therein. A second layer is comprised of a polyimide resin (92%) having an anti-thrombotic agent (6%) and an anti-microbial agent (2%) suspended therein.

According to a seventh example (not shown), the composite thermoset polymer matrix tube of the sixth example is cured over and around a braided transmission or reinforcing element as disclosed in previously incorporated U.S. Ser. No. 09/387,528, or over and around a spiral-wound conductor or reinforcing element as disclosed in previously incorporated U.S. Pat. No. 5,630,806.

There have been described and illustrated herein several embodiments of a composite thermoset polymer matrix structure and methods of forming the same. While particular embodiments of the invention have been described, it is not intended that the invention be limited thereto, as it is intended that the invention be as broad in scope as the art will allow and that the specification be read likewise. Thus, it will be appreciated that where a composite thermoset polymer matrix tape, wire coating, sheet, and tube have been disclosed, other structures may be formed as well. Further, it will be appreciated that the composite thermoset polymer resin matrix may be formed into any size structure as well. It will further be appreciated that the arrangement and composition of the cross-linked, adhesion, and hydrogen bonded polymer matrix layers may be varied depending upon the desirable qualities, properties, or characteristics required by the intended application. Also while particular examples having multiple layers with a plurality of resin/agent combinations exhibiting certain desirable properties or combinations of desirable properties were disclosed, it is understood that variations of those resin/agent combinations may likewise be formed depending upon particular requirements. Further, while the starting component for the thermoset polymer resin was disclosed as preferably being in liquid form for receiving the additive agent, both the thermoset resin and additive agent may be in particulate form upon mixing and then the thermoset resin may be converted to a liquid form prior to the forming of the structure. It will therefore be appreciated by those skilled in the art that yet other modifications could be made to the provided invention without deviating from its spirit and scope as claimed.

What is claimed is:

1. A composite thermoset polymer matrix structure comprising:

a) a first layer comprising a suspension of a first thermoset polymer resin and a first additive agent heterogeneously disposed but substantially evenly mixed within said first thermoset polymer resin, said first layer being cured such that said first layer is substantially a solid; and b) a second layer comprising a suspension of a second thermoset polymer resin and a second additive agent different from said first additive agent, said second additive agent heterogeneously disposed but substantially evenly mixed within said second thermoset polymer resin, said second layer being cured such that said second layer is substantially a solid and is homogeneously bonded to said first layer.

2. A composite thermoset polymer matrix structure according to claim 1, wherein:

said first thermoset polymer resin and said second thermoset polymer resin are selected from a group consisting of polyimide, polyurethane, polyester, polyamide-imide, and polyamide.

3. A composite thermoset polymer matrix structure according to claim 2, wherein:

said first and said second thermoset polymer resins are identical.

4. A composite thermoset polymer matrix structure according to claim 2, wherein:

said first and said second thermoset polymer resins are polyimide.

5. A composite thermoset polymer matrix structure according to claim 1, wherein:

said first additive agent and said second additive agent are selected from a group consisting of an anti-microbial agent, an anti-fungal agent, an anti-viral agent, an anti-thrombotic agent, a friction reducing agent, a radiopaque agent, and an electrically conductive agent.

6. A composite thermoset polymer matrix structure according to claim 5, wherein:

said anti-microbial agent is selected from a group of metal ion producing agents consisting of a silver ion producing agent, a zinc ion producing agent, a copper ion producing agent, and a gold ion producing agent.

7. A composite thermoset polymer matrix structure according to claim 6, wherein:

said metal ion producing agent releases silver ions in an aqueous environment, and is selected from a group consisting of zeolite, hydroxyl apatite, silica gel, glass, magnesium, aluminate silicate, and partially soluble phosphates.

8. A composite thermoset polymer matrix structure according to claim 6, wherein:

said anti-microbial agent is zeolite.

9. A composite thermoset polymer matrix structure according to claim 5, wherein:

said anti-thrombotic agent is selected from a group consisting of anti-thrombotic agents including heparin, phosphorylcholine, ibuprofen, acetylsalicylic acid, dipyridamole, indomethacin, prostaglandin, sulfinpyrazone, and warfarin.

10. A composite thermoset polymer matrix structure according to claim 5, wherein:

said friction reducing agent is one of polytetrafluoroethylene (PTFE), fluorinated ethylene propylene (FEP), and graphite.

11. A composite thermoset polymer matrix structure according to claim 5, wherein:

said radiopaque agent is selected from a group which provides x-ray visibility consisting of metallic tungsten, metallic barium, and metallic gold.

12. A composite thermoset polymer matrix structure according to claim 5, wherein:

said electrically conductive agent is selected from a group which dissipates static charges and shields against electromagnetic interference consisting of carbon black and graphite.

13. A composite thermoset polymer matrix structure according to claim 1 wherein:

said additive agent is in powder form having a powdered particulate size of up to 5 microns.

14. A composite thermoset polymer matrix structure according to claim 13, wherein:

said powdered particulate size is up to approximately 1 micron.

15. A composite thermoset polymer matrix structure according to claim 1, wherein:

said first additive agent constitutes up to 30% by weight of said first layer.

16. A composite thermoset polymer matrix structure according to claim 1, wherein:

at least one of said first layer and said second layer is comprised of a plurality of sublayers.

17. A composite thermoset polymer matrix structure according to claim 16, wherein:

a thickness of each of said plurality of sublayers is between 0.00025 and 0.05 inches.

18. A composite thermoset polymer matrix structure according to claim 1, wherein:

said structure is a tube.

19. A composite thermoset polymer matrix structure according to claim 1, wherein:

said structure is a sheet.

20. A composite thermoset polymer matrix structure according to claim 1, further comprising:

c) an adhesive layer disposed on one of said first and second layers, such that said first layer, said second layer and said adhesive layer together form an adhesive tape.

21. A composite thermoset polymer matrix structure according to claim 1, further comprising:

c) at least one additional layer of a thermoset polymer resin, said at least one additional layer cured as a solid, and homogeneously bonded to at least one of said first and second layers.

22. A composite thermoset polymer matrix structure according to claim 21, wherein:

said at least one additional layer further comprises an additive agent heterogeneously disposed but substantially evenly mixed within said thermoset polymer resin of said at least one additional layer.

23. A composite thermoset polymer matrix structure comprising:

a) a metal substrate;

b) a first layer comprising a first thermoset polymer resin, said first layer being cured such that said first layer is substantially solid and is disposed around said metal substrate; and c) a second layer comprising a second thermoset polymer resin and a first additive agent heterogeneously disposed but substantially evenly mixed within said second thermoset polymer resin, said second layer being cured such that said second layer is substantially a solid and is homogeneously bonded to said first layer and disposed around said first layer.

24. A composite thermoset polymer matrix structure according to claim 23, wherein:

said first thermoset polymer resin further comprises a second additive agent heterogeneously disposed but substantially evenly mixed within said first thermoset polymer resin, said second additive agent being different from said first additive agent.

25. A tubular structure, comprising:

a) a first layer comprising a suspension of a first thermoset polymer resin and a first additive agent heterogeneously disposed but substantially evenly mixed within said first thermoset polymer resin, said first layer being cured such that said first layer is substantially a solid; and b) a second layer comprising a second thermoset polymer resin, said second layer being cured such that said second layer is substantially a solid and is homogeneously bonded to said first layer, wherein said first and second layers together define a freestanding tubular structure having an open lumen.

26. A tubular structure according to claim 25, wherein:

said second layer is a suspension of said second thermoset polymer resin and a second additive agent different from said first additive agent, said second additive agent heterogeneously disposed but substantially evenly mixed within said second thermoset polymer resin.

27. A tubular structure according to claim 25, further comprising:

c) a third layer of a thermoset polymer resin, said third layer cured as a solid, and homogeneously bonded to at least one of said first and second layers.

28. A tubular structure according to claim 27, wherein:

said third layer further comprises an additive agent heterogeneously disposed but substantially evenly mixed within said thermoset polymer resin of said third layer.

29. A tubular structure according to claim 25, wherein:

said first and second thermoset polymer resins are polyimide.

30. A tubular structure according to claim 25, wherein:

said first additive agent is in powdered particulate form.

31. A tubular structure according to claim 26, wherein:

said first additive agent and said second additive agent are selected from a group consisting of an anti-microbial agent, an anti-fungal agent, an anti-viral agent, an anti-thrombotic agent, a friction reducing agent, a radiopaque agent, and an electrically conductive agent.

32. An adhesive sheet structure, comprising:

a) a first layer comprising a suspension of a first thermoset polymer resin and a first additive agent heterogeneously disposed but substantially evenly mixed within said first thermoset polymer resin, said first layer being cured such that said first layer is substantially a solid;

b) a second layer comprising a second thermoset polymer resin, said second layer being cured such that said second layer is substantially a solid and is homogeneously bonded to said first layer; and c) an adhesive layer disposed on one of said first and second layers.

33. An adhesive sheet structure according to claim 32, wherein:

said second layer is a suspension of said second thermoset polymer resin and a second additive agent different from said first additive agent, said second additive agent heterogeneously disposed but substantially evenly mixed within said second thermoset polymer resin.

34. An adhesive sheet structure according to claim 32, further comprising:

c) a third layer of a thermoset polymer resin, said third layer cured as a solid, and homogeneously bonded to at least one of said first and second layers.

35. An adhesive sheet structure according to claim 34, wherein:

said third layer further comprises an additive agent heterogeneously disposed but substantially evenly mixed within said thermoset polymer resin of said third layer.

36. An adhesive sheet structure according to claim 32, wherein:

said first and second thermoset polymer resins are polyimide.

37. An adhesive sheet structure according to claim 32, wherein:

said first additive agent is in powdered particulate form.

38. An adhesive sheet structure according to claim 33, wherein:

said first additive agent and said second additive agent are selected from a group consisting of an anti-microbial agent, an anti-fungal agent, an anti-viral agent, an anti-thrombotic agent, a friction reducing agent, a radiopaque agent, and an electrically conductive agent.

* * * * *